United States Patent
Tierney et al.

(10) Patent No.: US 8,987,246 B2
(45) Date of Patent: Mar. 24, 2015

(54) METHODS FOR TREATMENT OF AUTISM SPECTRUM DISORDER

(71) Applicants: The Johns Hopkins University, Baltimore, MD (US); Kennedy Krieger Institute, Inc., Baltimore, MD (US); National Institutes of Health, Bethesda, MD (US)

(72) Inventors: Elaine Tierney, Silver Spring, MD (US); Forbes D. Porter, Bethesda, MD (US)

(73) Assignees: The Johns Hopkins University, Baltimore, MD (US); Kennedy Krieger Institute, Inc., Baltimore, MD (US); National Institutes of Health, Bethesda, MD (US)

( * ) Notice: Subject to any disclaimer, the term of this patent is extended or adjusted under 35 U.S.C. 154(b) by 0 days.

(21) Appl. No.: 13/945,384

(22) Filed: Jul. 18, 2013

(65) Prior Publication Data

US 2014/0024632 A1    Jan. 23, 2014

Related U.S. Application Data

(60) Provisional application No. 61/672,933, filed on Jul. 18, 2012.

(51) Int. Cl.
*A61K 31/555* (2006.01)
*A61K 31/575* (2006.01)

(52) U.S. Cl.
CPC .................................. *A61K 31/575* (2013.01)
USPC ...................................................... 514/187

(58) Field of Classification Search
CPC .................................................. A61K 31/575
USPC ......................................................... 514/182
See application file for complete search history.

(56) References Cited

PUBLICATIONS

Lee, R., et al., "Hypothesis: the role of sterols in autism spectrum disorder", Autism Research and Treatment (2011), vol. 2011, Article ID 653570, pp. 1-7.
Aneja, A., et al., "Autism: the role of cholesterol in treatment", International Review of Psychiatry, Apr. 2008; vol. 20, No. 2, pp. 165-170.
Tierney, E., et al., "Abnormalities of cholesterol metabolism in autism spectrum disorders", American Journal of Medical Genetics Part B (Neuropsychiatric Genetics) (2006); 141B:666-668.
Tierney, E., et al., "Behavior Phenotype in the RSH/Smith-Lemli-Opitz Syndrome", American Journal of Medical Genetics (2001) vol. 98, pp. 191-200.
Sikora, D., et al., "The near universal presence of autism spectrum disorders in children with smith-lemli-opitz syndrome", American Journal of Medical Genetics Part A (2006), 140A:1511-1518.

*Primary Examiner* — Jennifer M Kim
(74) *Attorney, Agent, or Firm* — Johns Hopkins Technology Transfer (57) ABSTRACT

The present invention relates to the field of autism. More specifically, the present invention provides methods for treating individuals with autism spectrum disorder. Accordingly, in one aspect, the present invention provides methods for treating patients with autism spectrum disorder. In one embodiment, a method for treating an autism spectrum disorder (ASD) in a patient comprises the step of administering a therapeutically effective amount of cholesterol to the patient. In more specific embodiments, the ASD is autism, Asperger's disorder, pervasive developmental disorder-not otherwise specified (PDD-NOS), Rett's syndrome and childhood disintegrative disorder. In one embodiment, the patient has autism.

14 Claims, 7 Drawing Sheets

CORRELATION MATRIX BETWEEN VARIABLES

|          | repetdd | nonverbal | verbal  | social  | age    | chol   | agechol |
|----------|---------|-----------|---------|---------|--------|--------|---------|
| repetdd  | 1.0000  |           |         |         |        |        |         |
|          | 18      |           |         |         |        |        |         |
| nonverbal| 0.1307  | 1.0000    |         |         |        |        |         |
|          | 0.6051  |           |         |         |        |        |         |
|          | 18      | 18        |         |         |        |        |         |
| verbal   | 0.1954  | 0.9817| 1.0000  |         |        |        |         |
|          | 0.5427  | 0.0000|         |         |        |        |         |
|          | 12      | 12        | 12      |         |        |        |         |
| social   | 0.3449  | 0.7724| 0.8466 | 1.0000 |        |        |         |
|          | 0.1610  | 0.0002| 0.0005 |        |        |        |         |
|          | 18      | 18        | 12      | 18      |        |        |         |
| age      | -0.4944 | 0.0106 | -0.5618 | -0.4497 | 1.0000 |        |         |
|          | 0.0370  | 0.9667 | 0.0573  | 0.0612  |        |        |         |
|          | 18      | 18        | 12      | 18      | 18     |        |         |
| chol     | -0.0172 | -0.4800 | -0.6990 | -0.6235 | 0.4289 | 1.0000 |     |
|          | 0.9460  | 0.0438  | 0.0114  | 0.0057  | 0.0757 |        |     |
|          | 18      | 18        | 12      | 18      | 18     | 18     |         |
| agechol  | -0.3852 | 0.3805    | -0.1952 | -0.0235 | 0.6412 | 0.0000 | 1.0000 |
|          | 0.1145  | 0.1193    | 0.5432  | 0.9263  | 0.0041 | 1.0000 |        |
|          | 18      | 18        | 12      | 18      | 18     | 18     | 18      |

METHODS FOR TREATMENT OF AUTISM SPECTRUM DISORDER

CROSS-REFERENCE TO RELATED APPLICATIONS

This application claims the benefit of U.S. Provisional Application No. 61/672,933, filed Jul. 18, 2012; which is incorporated herein by reference in its entirety.

FIELD OF THE INVENTION

The present invention relates to the field of autism. More specifically, the present invention provides methods for treating individuals with autism spectrum disorder.

BACKGROUND OF THE INVENTION

The autism spectrum disorders (ASD) affect as many as 1 in 88 children in the United States and comprise a broad group of behaviorally related neurodevelopmental disorders that include autism, Asperger's disorder, pervasive developmental disorder-not otherwise specified (PDD-NOS), Rett's syndrome and childhood disintegrative disorder. The hallmark features of ASD appear around three years of age as impaired social and communication interactions, pronounced repetitive behaviors and restricted pattern of interests. There continues to be a need for treatments for autistic individuals.

SUMMARY OF THE INVENTION

The present invention is based, at least in part, on the discovery that a subgroup of children with autism spectrum disorders (ASD) has low cholesterol. The present inventors hypothesize that cholesterol and other sterol abnormalities may play a role in the cause of one or more subtypes of ASD. As described herein, three clinical sites collaborate to determine the frequency of very low cholesterol (hypocholesterolemia) in ASD. Sixty children (20 at each site) with ASD and low cholesterol receive supplemental cholesterol or placebo over 13 weeks in a controlled (placebo double-masked) trial. The outcome is assessed by standard clinical rating scales designed to measure a range of behavioral and communicative functions.

The clinical trial is designed to determine the frequency and clinical features of sterol disorders in ASD, including behavior, appearance, intelligence, and language. In addition, the trial is designed to treat individuals with ASD who have very low cholesterol blood levels and monitor to see if these features improve. For people with ASD, the present invention provides the essential evidence required to evaluate the potential of cholesterol supplementation in the treatment of the core symptoms of ASD in youths with ASD and low cholesterol.

Accordingly, in one aspect, the present invention provides methods for treating patients with autism spectrum disorder. In one embodiment, a method for treating an autism spectrum disorder (ASD) in a patient comprises the step of administering a therapeutically effective amount of cholesterol to the patient. In more specific embodiments, the ASD is autism, Asperger's disorder, pervasive developmental disorder-not otherwise specified (PDD-NOS), Rett's syndrome and childhood disintegrative disorder. In one embodiment, the patient has autism. In certain embodiments, the therapeutically effective amount of cholesterol is about 20 to about 300 mg/Kg body weight/day. In another embodiment, the patient does not have Smith-Lemli-Opitz syndrome (SLOS). In yet another embodiment, the patient has clinically low levels of cholesterol. In a further embodiment, the patient has normal cholesterol levels.

In another embodiment, a method for treating a patient having ASD but not SLOS comprises the step of administering a therapeutically effective amount of cholesterol to the patient. In a specific embodiment, the patient has clinically low levels of cholesterol. In another embodiment, the patient has normal cholesterol levels. In yet another embodiment, a method for treating a patient having ASD, normal cholesterol levels, and who does not have SLOS comprises the step of administering a therapeutically effective amount of cholesterol to the patient. In a further embodiment, a method for treating a patient having ASD, low cholesterol levels, and who does not have SLOS comprises the step of administering a therapeutically effective amount of cholesterol to the patient. In such embodiments, the ASD is autism, Asperger's disorder, pervasive developmental disorder-not otherwise specified (PDD-NOS), Rett's syndrome and childhood disintegrative disorder. In particular embodiments, the patient has autism. In certain embodiments, the therapeutically effective amount of cholesterol is about 20 to about 300 mg/Kg body weight/day.

In one embodiment, a method for treating a patient suffering from autism but not SLOS comprises the step of administering a therapeutically effective amount of cholesterol to the patient. In other embodiments, the patient has clinically low levels of cholesterol. In certain embodiments, the patient has normal cholesterol levels. In another embodiment, a method for treating a patient who has autism, normal cholesterol levels, and who does not have SLOS comprises the step of administering a therapeutically effective amount of cholesterol to the patient. In yet another embodiment, a method for treating a patient who has autism, low cholesterol levels, and who does not have SLOS comprises the step of administering a therapeutically effective amount of cholesterol to the patient. In certain embodiments, the therapeutically effective amount of cholesterol is about 20 to about 300 mg/Kg body weight/day.

DETAILED DESCRIPTION OF THE INVENTION

It is understood that the present invention is not limited to the particular methods and components, etc., described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to a "protein" is a reference to one or more proteins, and includes equivalents thereof known to those skilled in the art and so forth.

Unless defined otherwise, all technical and scientific terms used herein have the same meaning as commonly understood by one of ordinary skill in the art to which this invention belongs. Specific methods, devices, and materials are described, although any methods and materials similar or equivalent to those described herein can be used in the practice or testing of the present invention.

All publications cited herein are hereby incorporated by reference including all journal articles, books, manuals, published patent applications, and issued patents. In addition, the meaning of certain terms and phrases employed in the specification, examples, and appended claims are provided. The definitions are not meant to be limiting in nature and serve to provide a clearer understanding of certain aspects of the present invention.

The present inventors hypothesize that altered cholesterol metabolism or elevated dehydrocholesterol levels are a contributing factor in some individuals with autism spectrum disorder (ASD) and that therapeutic cholesterol treatments might also impact ASD associated with sterol disorders that is not due to SLOS.

Evidence for the role of low cholesterol in causing a subtype of ASD comes from five sources. First, fifty percent of individuals with Smith-Lemli-Opitz Syndrome (SLOS) meet the behavioral criteria for autistic disorder (Tierney et al., 98 AM. J. MEDICAL GENETICS 191-200 (2001)) and 75% meet the criteria for ASD (Sikora et al., 140 AM. J. MED. GENET. PART A 1511-18 (2006)). Second, in individuals with SLOS, the lower the blood and cerebrospinal fluid was, the more severe were the autism, IQ, and adaptive function deficits. Third, in SLOS, improvement was found in social and communication abilities with cholesterol supplementation. Fourth, cholesterol was low in a pilot study of 200 children with idiopathic ASD i.e., ASD of unknown cause (Tierney et al, 141B AM. J. MEDICAL GENETICS PART B 666-68 (2006)). Fifth, it is becoming increasingly clear that cholesterol plays a pivotal role in several aspects of brain development.

SLOS is Caused by Impaired Cholesterol Synthesis. Smith-Lemli-Opitz syndrome (SLOS) is an autosomal-recessive syndrome caused by an enzyme deficiency in the last step in cholesterol biosynthesis. This enzyme, called 7-dehydrocholesterol reductase (DHCR7), converts a precursor sterol called 7-dehydrocholesterol (7DHC) to cholesterol. In individuals with SLOS, this enzyme is either absent or functions abnormally. As a result, insufficient cholesterol is produced in the body and 7DHC accumulates. Principal abnormalities include a typical facial appearance, microcephaly, hypotonia, cleft palate, 2-3 toe syndactyly, and a characteristic behavioral profile. Due to hedgehog protein signaling abnormalities that are secondary to inadequate availability of cholesterol and possibly other sterol metabolites, structural central nervous system (CNS) abnormalities are seen in individuals with SLOS. The enzyme abnormality in SLOS affects the synthesis and metabolism of sterol-derived compounds, including bile acids, oxysterols, adrenal steroids, and neuroactive steroids. This genetic defect also affects normal function of cholesterol-rich membranes that are involved in signal transduction, synapse formation, and myelination.

The clinical incidence of SLOS is approximately 1 in 50,000 births, and the carrier frequency is at least 1%. The discrepancy between the high carrier frequency and the number of identified cases suggested the possibility that mild cases may not be completely ascertained. The clinical manifestations of SLOS are extremely variable. Milder cases of SLOS combine minor physical stigmata with behavioral difficulties, learning disabilities and ASD. The SLOS Physical Severity Scale (SLOS-PSS) was created for the clinical assessment of individuals with SLOS and SLOS-PSS scores have been found to significantly correlate with the sterol levels.

Dietary Cholesterol Supplementation is the Standard Clinical Treatment for SLOS. The current recommended treatment for SLOS is to begin dietary cholesterol supplementation as soon as this condition is diagnosed. Individuals with SLOS have significant irritability; sleep disturbance and obsessive compulsive behavior, which improve with cholesterol supplementation. The behavioral profile of SLOS has several features, such as excessive anxiety, that would be expected in a GABA-deficiency syndrome. Some reports suggest that cholesterol supplementation improves growth, speech articulation and neurodevelopmental status. Although one group found that their developmental status did not improve over time with cholesterol supplementation; behavioral aspects of SLOS were not studied.

Cholesterol is Essential to Multiple Biomechanisms. Cholesterol has multiple biological functions, some of which could plausibly contribute to ASD. Cholesterol is an important building block for the body's cell membranes, for myelination of the central nervous system, and a major component of lipid rafts. Lipid rafts are subcellular structures that function in many signal transduction systems including neuronal transmission. In its role as a component of lipid rafts, cholesterol modulates the ligand binding activity and G-protein coupling of the serotonin1A (5-HT1A) receptor.

Cholesterol is the precursor for neurosteroid production. The defect in cholesterol synthesis in SLOS may lead to abnormal neurosteroid production. There is evidence of decreased neurosteroid levels, dehydroepiandrosterone (DHEA) and DHEA-sulfate (DHEA-S) in adults with autistic disorder. Neurosteroids exhibit a wide range of modulatory effects on neurotransmitter receptor activity and exhibit neurodevelopmental and neuroprotective effects, and a deficit may be associated with mood and anxiety disorders. Neurosteroids also promote dendritic growth, spinogenesis and synaptogenesis via receptors in the Purkinje cell.

Hypocholesterolemia and Hypercholesterolemia have been Associated with ASD. Over half of the 17 subjects in the present inventors' first study with SLOS met Autism Diagnostic Interview (ADI-R) and DSM-IV diagnostic criteria for autism, and in another study of 14 SLOS subjects, approximately three-fourths (71-86% depending upon the evaluation method) met criteria for some variant of ASD with 50% having met the criteria for autism, suggesting a consistent relationship with ASD and this single-gene disorder. In 100 ASD Autism Genetic Resource Exchange study participants who had a sibling with ASD (from a multiplex family), 19% had levels of cholesterol below 100 mg/dL, lower than the 5th centile. The value of 100 mg/dL was used because the authors did not yet know of the CDC NHANES normative data. Of note, one research group reported that total cholesterol and low density lipoprotein (LDL) levels were significantly higher in 22 individuals with Asperger disorder than in 22 well matched controls after accounting for lifestyle variables.

The understanding of the pivotal role that cholesterol plays in multiple components of the central nervous system (CNS)

is occurring at the same time that researchers are investigating whether the structural CNS and behavioral features of subjects with SLOS resemble those with ASD of unknown etiology. SLOS sterol abnormalities affect the synthesis and metabolism of sterol-derived compounds, including bile acids and adrenal steroids and the present inventors have hypothesized that SLOS-related deficits may affect neuroactive steroids and neurosteroids, the structure of sterol-rich membranes, such as myelin, and the proper functioning of serotonin and other brain receptors.

Thus, the present inventors have been studying the relationship between autism and low cholesterol, first in children with SLOS, and then in children with idiopathic autism from multiplex families.

Cholesterol Supplementation Improved Behavioral Symptoms and May Improve ASD Features in SLOS. The Autism Diagnostic Interview was conducted with 6 SLOS individuals, and data was obtained for 3 "current state" time-points: age 4-5, just before starting cholesterol supplementation, and present while on cholesterol. The change in the score of three ADI algorithm domains—Social, Communication, and Restricted, Repetitive, and Stereotyped Behavior—was estimated. Because the time between visits varied from subject to subject, a model was developed to control for age and time lapse between tests. A detailed description of the model and outcomes is included in Example 1. In summary, on the Social domain, the individuals on cholesterol supplementation improved by an average of 7.07 points more than children not on supplementation (p value 0.008). The ADI Communication domain has a non-verbal score that is completed for all individuals and a verbal score that is completed in those individuals who have phrase speech. The value for the non-verbal score is within the verbal total score. In the non-verbal children, the language domain score improved 2.51, p value 0.04. In the verbal children, the verbal score had an increase at an average of 6.97 points (p value<0.001). In the Repetitive domain, the children worsened an average of 1.54 points (p value<0.001) (Example 1).

Low Plasma and Low Cerebrospinal Fluid Sterol Levels Correlate Significantly with Behavioral Characteristics in SLOS. Fifteen subjects with SLOS participated in an Autism Speaks-funded double-blind placebo-controlled clinical trial of simvastatin. This is a treatment that is usually used for lowering cholesterol but is expected to increase cholesterol production in mildly affected individuals with SLOS. The baseline levels of sterols in the cerebrospinal fluid and plasma were those measured while the subjects were on cholesterol supplementation, but not yet on simvastatin. Linear regression analyses were performed with the CSF and plasma sterols levels and the behavioral measures listed below, and the results are detailed in Table 2 of Example 1, with the p-values reflecting Bonferonni correction for multiple comparisons in the sub domains of the ADI, ADOS, and IQ, and is summarized below.

The Autism Diagnostic Observation Schedule-Generic (ADOS-G) was used to measure current social and language behavior. The ADOS has 4 versions or modules, depending on the subject's age and language ability. While some items differ across modules, many are common across modules. The ADOS scores of total score and imagination play significantly correlated with both the Plasma and CSF 7DHC, 8DHC, and ratio of 7DHC to total sterols (ratio), and demonstrated that the higher the impairment in sterol metabolism at DHCR7, the greater the impairment on the ADOS.

The ADI algorithm was used as a measure of autism features, with all scores of "3" maintained as a "3" for analyses purposes (not for diagnostic purposes). The Social domain and the Non-Verbal domain scores reflect the parent's answers regarding the child at 4.0 to 5.0 years, while the Repetitive Behavior domain primarily asks whether the behavior had ever occurred in the past. The Total score correlated significantly with both the Plasma and CSF 7DHC, 8DHC, and ratio values.

The ADI was also analyzed as a measure of current functioning. The majority of the ADI questions ask about the current state of the individual but with the Social domain and the Non-Verbal domain these answers do not go into the algorithm scores. In order to measure present functioning, after the ADI was administered, a few additional current state questions were asked of the parent. All scores of "3" were maintained as a "3." The Total score, Social Subscale and Non-Verbal Subscale scores correlated significantly with the Plasma and CSF 7DHC, 8DHC, and ratio. Of note, the significance of the p values obtained when the ADI algorithm was used for the usual time-points, but with 3s as 3s, was tenfold greater than the significance of the ADOS total score. Also, the Current State values, with 3s as 3s, had a tenfold greater significance than the usual time-point ADI algorithm scores with 3s as 3s.

The IQ was estimated using the Mullen Scales of Early Learning (Mullen) for nonverbal subjects and the Stanford-Binet Intelligence Scales-IV (SB-IV) for verbal subjects. The Mullen was used to calculate the Developmental Quotient by dividing the developmental age in months by the chronological age in months. A Full Scale IQ was determined by the SB-IV Full Scale IQ score in verbal individuals. In non-verbal individuals the Full Scale IQ was calculated by averaging 1) the Mullen Visual Receptive Score with 2) the Mullen Average of Receptive-Expressive DQ Score. The Mullen Visual Receptive Score is a measure of Non-verbal IQ. The Mullen Receptive & Mullen Expressive scores are combined to give the equivalent of a Verbal IQ with the SB-IV. There were significant correlations for both plasma and CSF with 7DHC, 8DHC, ratio, and cholesterol values.

The Vineland Scales of Adaptive Behavior (Vineland) (Sparrow et al., 1984) was obtained and plasma values correlated significantly across all sterol measurements, with the CSF values reaching significance in 7DHC and ratio.

Of 200 Autism Genetic Resource Exchange (AGRE) Multiplex ASD subjects, 23% had Hypocholesterolemia and 9% had Hypercholesterolemia. In order to determine whether mild SLOS is a significant etiologic factor contributing to ASD, the present inventors designed a study to use blood samples from AGRE to determine 1) the incidence of SLOS in a cohort of subjects from multiplex ASD families (multiplex means two or more first-degree relatives with ASD) (1 affected subject per family was included), and 2) whether or not other disorders of sterol metabolism might present as ASD. The samples were analyzed at Kennedy Krieger Institute (KKI) (Baltimore, Md.) and cholesterol and all post-squalene sterol precursors were identified and quantified by gas chromatography/mass spectrometry.

Figure 1:
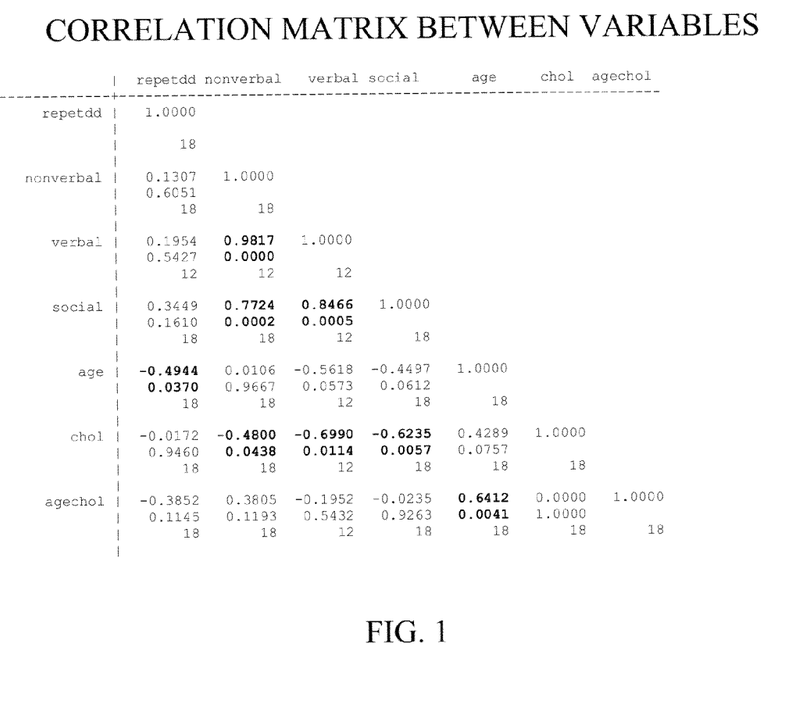
FIG. 1. Correlation matrix between variables. Social, verbal, and nonverbal scores all appear to be measuring the same thing, but repetitive behaves quite differently. Cholesterol supplementation is strongly associated with social, verbal, and non-verbal scores: for children who have already begun supplementation, scores tend to be lower on average (this does not account for age or other factors). Age and repetitive score are associated, suggesting that as children get older, their repetitive scores decline.
Figure 2:
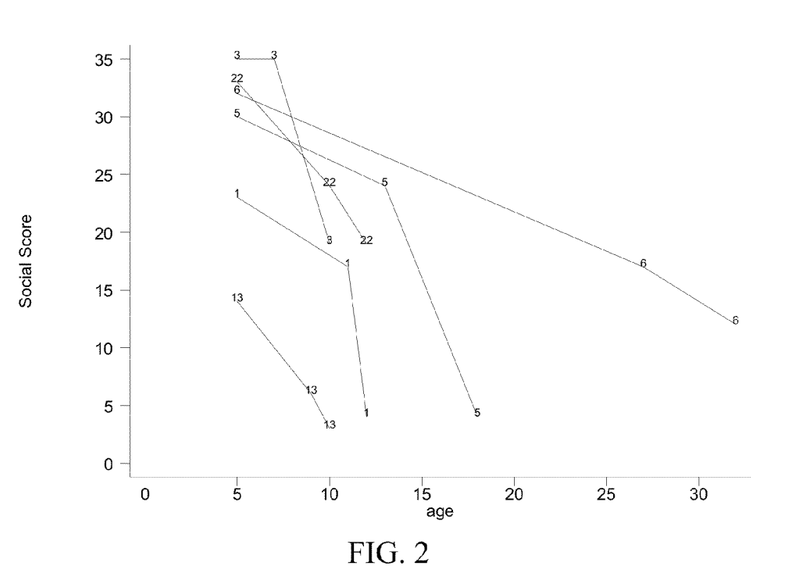
FIG. 2. Graph of age vs. social score.
Figure 3:
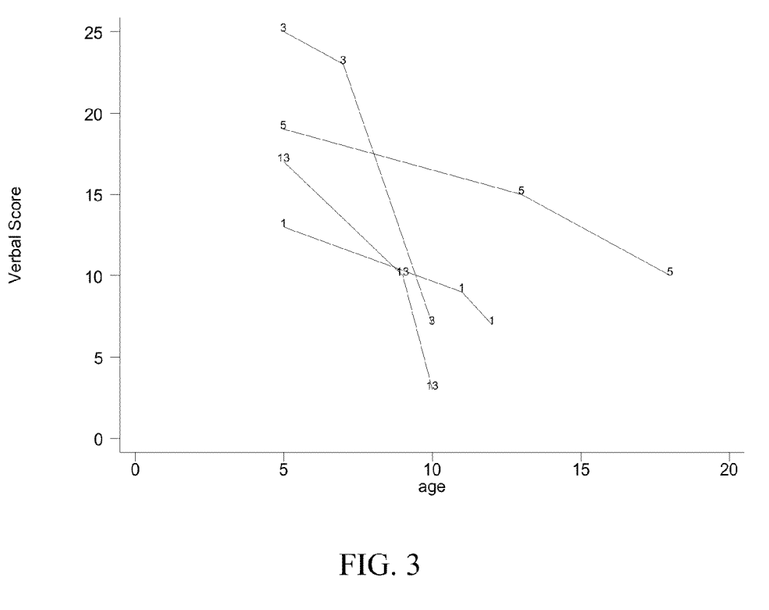
FIG. 3. Graph of age vs. verbal score.
Figure 4:
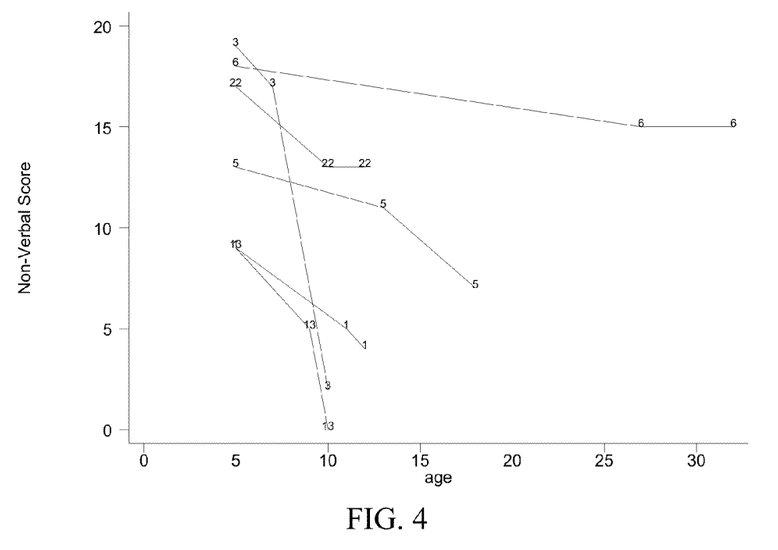
FIG. 4. Graph of age vs. non-verbal score.
Figure 5:
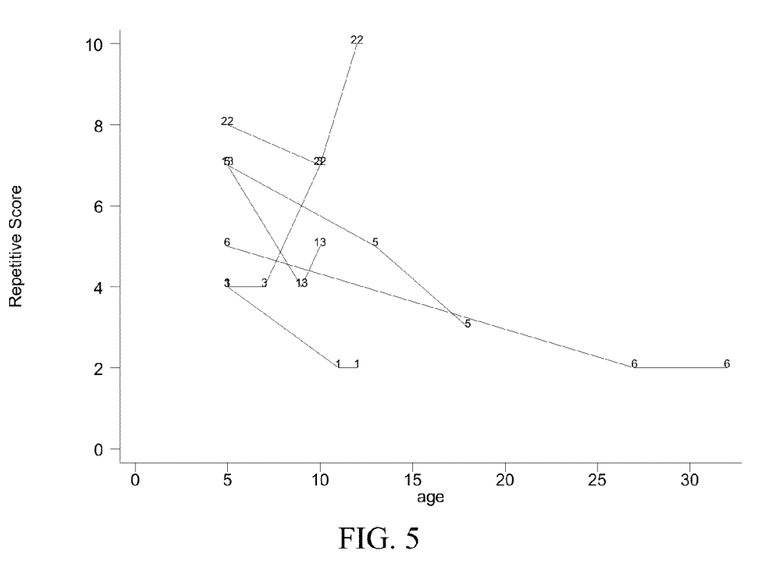
FIG. 5. Graph of age vs. repetitive score.
Figure 6:
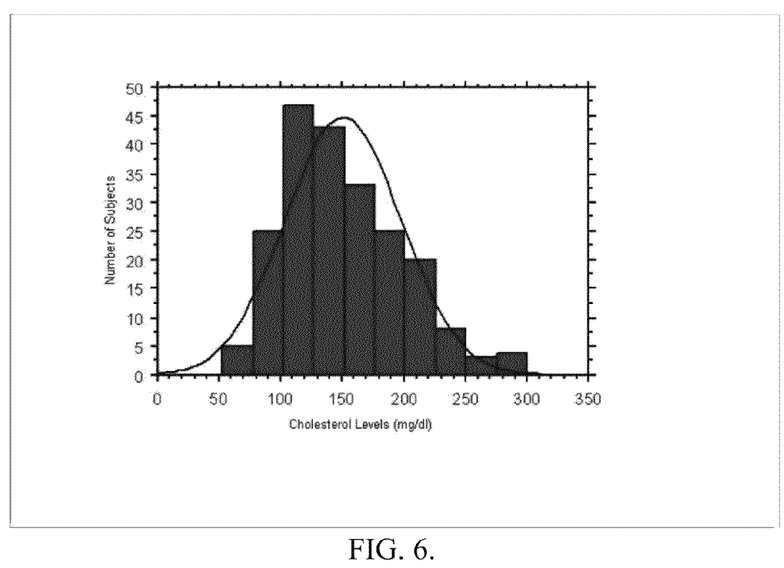
FIG. 6. Distribution of cholesterol levels in 200 AGRE multiplex subjects.
Figure 7:
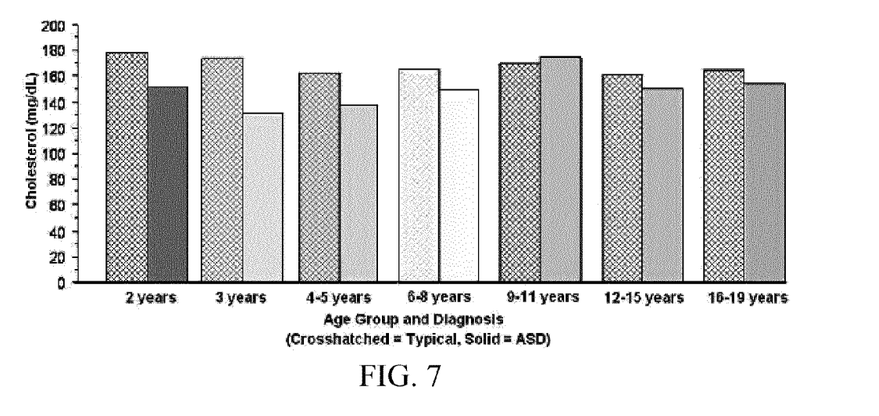
FIG. 7. Mean cholesterol blood levels in the typical population* and 200 AGRE multiplex subject, divided by age segment.

None of the 200 AGRE samples had a finding consistent with SLOS or abnormal level of any other sterol precursor of cholesterol. FIG. 6 shows the distribution of cholesterol levels of the 200 AGRE subjects. FIG. 7 shows the distribution of cholesterol levels across the age range: the cholesterol levels were elevated in comparison the NHANES cohort across almost the entire age span.

Of the initial group of 100 samples, 19 had a total cholesterol level lower than 100 mg/d, which is below the 1st centile for youths over the age of 2 years for cholesterol levels matched by age and gender, and 33% had a value that was at the 2.28$^{th}$ centile or lower (CDC National Health and Nutrition Examination Survey: NHANES).

The 100 AGRE individuals with a cholesterol level below 100 mg/dl, had a statistically lower level of lathosterol compared to the entire group, indicating that the cause of the hypocholesterolemia was decreased cholesterol synthesis rather than increased cholesterol losses from gastrointestinal disturbances or abnormal diets.

In an expanded population 200 AGRE samples, 29 (14.5%) had cholesterol levels lower than 100 mg/dl and 45 (23%) had levels at the 2.28$^{th}$ centile or lower (10 times greater than the typical population). In addition, 5 additional subjects missed that cut-off by 1 mg/dl.

In the combined group of 200, there were significantly more "Broad spectrum" (BS) and "not quite autism" (NQA) classifications in the hypocholesterolemic subjects than in the remaining cholesterol groups (chi-square 12.95, chi square p-value 0.04). Of those 19 individuals in the low cholesterol group, 6 met BS criteria rather than autism criteria; while, of the 81 individuals with higher cholesterol levels, 8 met BS criteria.

NQA is defined as being one point away from meeting autism criteria on any or all of the social, communication, and/or behavior domains, and either meets criteria on the "age of onset" domain, or meets criteria on all three domains, but does not meet criteria on the "age of onset" domain. BS shows patterns of impairment within the spectrum of pervasive developmental disorders.

There was no association between having an abnormally low cholesterol level and the a history of regression of milestones in either group of 100 subjects, when regression was defined as the parent giving an answer that led to a score of "1" or "2" on ADI-R question number 95a, version 1995.

These markedly elevated rates of hypocholesterolemia in a multiplex ASD population that also showed a pattern that indicated the low cholesterol levels were due to decreased cholesterol synthesis suggest that genetic factors influencing sterol metabolism may be contributing to the pathophysiology of ASD.

I. Definitions

The following definitions are used throughout this specification. Other definitions are embedded within the specification for ease of reference.

As used herein, the term "effective," means adequate to accomplish a desired, expected, or intended result. More particularly, a "therapeutically effective amount" as provided herein refers to an amount of a cholesterol supplement of the present invention, either alone or in combination with another therapeutic agent (e.g., a cholesterol marker and/or a different therapeutic agent), necessary to provide the desired therapeutic effect, e.g., an amount that is effective to prevent, alleviate, or ameliorate symptoms of ASD. In a specific embodiment, the term "therapeutically effective amount" as provided herein refers to an amount of a cholesterol, necessary to provide the desired therapeutic effect, e.g., an amount that is effective to prevent, alleviate, or ameliorate symptoms of ASD. In more specific embodiments, a therapeutically effective amount of a cholesterol supplement refers to an amount necessary to treat or prevent ASD including, but not limited to, autism, Asperger's disorder, PDD-NOS, Rett's syndrome and childhood disintegrative disorder.

As would be appreciated by one of ordinary skill in the art, the exact amount required will vary from subject to subject, depending on age, general condition of the subject, the severity of the condition being treated, the particular cholesterol compound and/or composition administered, and the like. An appropriate "therapeutically effective amount" in any individual case can be determined by one of ordinary skill in the art by reference to the pertinent texts and literature and/or by using routine experimentation.

The terms "sample," "patient sample," "biological sample," and the like, encompass a variety of sample types obtained from a patient, individual, or subject and can be used in a diagnostic or monitoring assay. The patient sample may be obtained from a healthy subject, a patient having an ASD or a patient having associated symptoms of an ASD. Moreover, a sample obtained from a patient can be divided and only a portion may be used for diagnosis. Further, the sample, or a portion thereof, can be stored under conditions to maintain sample for later analysis. The definition specifically encompasses blood and other liquid samples of biological origin (including, but not limited to, peripheral blood, serum, plasma, cerebrospinal fluid, urine, saliva, stool and synovial fluid), solid tissue samples such as a biopsy specimen or tissue cultures or cells derived therefrom and the progeny thereof. In a specific embodiment, a sample comprises a blood sample. In another embodiment, a sample comprises a plasma sample. In yet another embodiment, a serum sample is used.

As used herein, the terms "treatment," "treating," and the like, refer to obtaining a desired pharmacologic and/or physiologic effect. The effect may be prophylactic in terms of completely or partially preventing an ASD or symptom thereof and/or may be therapeutic in terms of a partial or complete cure for an ASD or condition and/or adverse affect attributable to the disease or condition. "Treatment," as used herein, covers any treatment of an ASD or condition in a subject, particularly in a human, and includes: (a) preventing the ASD or condition from occurring in a subject which may be predisposed to the ASD but has not yet been diagnosed as having it; (b) inhibiting the ASD or condition, i.e., arresting its development; and (c) relieving the ASD or condition, e.g., causing regression of the ASD or condition, e.g., to completely or partially remove symptoms of the ASD or condition.

II. Cholesterol Testing

In certain embodiments, a patient sample may be tested to determine whether cholesterol deficiency or abnormalities in cholesterol transport are present. Cholesterol markers or panels are known to those of ordinary skill in the art. One or more markers can be analyzed including, total cholesterol, apolipoprotein A-l, apolipoprotein B, Lipoprotein (a), and homocysteine.

Total cholesterol: Total cholesterol measures all types of cholesterol including esterified and free. Low values (generally values less than about 160 mg/dL) are associated with genetic diseases of cholesterol metabolism such as SLOS, Tangier's disease, and abetalipoproteinemia. Low values are more common in hyperthyroidism, liver disease, malabsorption, malnutrition, violent behavior, celiac disease, anxiety, bipolar disease, alcoholism, lung cancer, suicide, depression, and obesity associated with human adenovirus-36 infection. High cholesterol values are associated with atherosclerosis.

Apolipoprotein A-I (Apo A-l): The main protein component of HDL (high density lipoprotein). It accounts for approximately 65% of the total protein content of HDL. Apo A-I activates lecithin cholesterol acyltransferase which catalyzes the esterification of cholesterol. The resulting esterified cholesterol can then be transported to the liver, metabolized and excreted. Values of Apo A-I have been shown to decrease during infection.

Apolipoprotein B (Apo B): The main protein component of LDL (low density lipoprotein). It accounts for approximately 95% of the total protein content of LDL. Apolipoprotein B is necessary for the reaction with LDL receptors in the liver and on cell walls and is thus involved in transporting cholesterol from the liver to the cells. Recently the Mind Institute found that low values of Apo B are associated with autism, with the lowest values being found in low-functioning autism. LDL has found to have protective effects against endotoxins from deadly *staphylococcus*.

Lipoprotein (a): Consists of two components, the low-density lipoprotein (LDL) and a glycoprotein, which are linked by a disulfide bridge. High values have been implicated as a risk factor for cardiovascular disease, Alzheimer's disease, Crohn's disease, and rheumatoid arthritis. Low values have also been found in those with autism who have higher doses of Apolipoprotein E epsilon-4 gene variants that are associated with increased risk of Alzheimer's disease. Lipoprotein (a) is biochemically unrelated to Apolipoprotein A.

Homocysteine: A sulfur-containing amino acid that can be converted to methionine by methionine synthetase or by betaine methyl transferase. The role of homocysteine in atherosclerosis gained attention after finding massive atherosclerosis in young people with the genetic disorder homocystinuria. Methionine synthetase requires the folic acid derivative 5-methyl tetrahydrofolate. Abnormally high values have been reported in stroke, cardiovascular disease, and in Alzheimer's disease. Both low and high values have been reported in autism.

III. Pharmaceutical Compositions Comprising Cholesterol

Accordingly, a pharmaceutical composition of the present invention may comprise an effective amount of cholesterol. Cholesterol supplements are commercially available. See, e.g., SLOesterol™ (Solace Nutrition (Pawcatuck, Conn.)) As used herein, the term "effective," means adequate to accomplish a desired, expected, or intended result. More particularly, an "effective amount" or a "therapeutically effective amount" is used interchangeably and refers to an amount of at least one cholesterol marker, perhaps in further combination with yet another therapeutic agent, necessary to provide the desired "treatment" (defined herein) or therapeutic effect, e.g., an amount that is effective to prevent, alleviate, treat or ameliorate symptoms of ASD. In particular embodiments, the pharmaceutical compositions of the present invention are administered in a therapeutically effective amount to treat patients having an ASD including, but not limited to, autism, Asperger's disorder, PDD-NOS, Rett's syndrome and childhood disintegrative disorder. As would be appreciated by one of ordinary skill in the art, the exact cholesterol dose amount required will vary from subject to subject, depending on age, general condition of the subject, the severity of the condition being treated, the particular compound and/or composition administered, and the like. An appropriate "therapeutically effective amount" in any individual case can be determined by one of ordinary skill in the art by reference to the pertinent texts and literature and/or by using routine experimentation.

The pharmaceutical compositions of the present invention are in biologically compatible form suitable for administration in vivo for subjects. The pharmaceutical compositions can further comprise a pharmaceutically acceptable carrier. The term "pharmaceutically acceptable" means approved by a regulatory agency of the Federal or a state government or listed in the U.S. Pharmacopeia or other generally recognized pharmacopeia for use in animals, and more particularly, in humans. The term "carrier" refers to a diluent, adjuvant, excipient, or vehicle with which the TGF-beta inhibitor is administered. Such pharmaceutical carriers can be sterile liquids, such as water and oils, including those of petroleum, animal, vegetable or synthetic origin, including but not limited to peanut oil, soybean oil, mineral oil, sesame oil and the like. Water may be a carrier when the pharmaceutical composition is administered orally. Saline and aqueous dextrose may be carriers when the pharmaceutical composition is administered intravenously. Saline solutions and aqueous dextrose and glycerol solutions may be employed as liquid carriers for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried slim milk, glycerol, propylene, glycol, water, ethanol and the like. The pharmaceutical composition may also contain minor amounts of wetting or emulsifying agents, or pH buffering agents.

The pharmaceutical compositions of the present invention can take the form of solutions, suspensions, emulsions, tablets, pills, capsules, powders, sustained-release formulations and the like. The composition can be formulated as a suppository, with traditional binders and carriers such as triglycerides. Oral formulation may include standard carriers such as pharmaceutical grades of mannitol, lactose, starch, magnesium stearate, sodium saccharine, cellulose, magnesium carbonate, etc. In a specific embodiment, a pharmaceutical composition comprises an effective amount of a TGF-beta inhibitor together with a suitable amount of a pharmaceutically acceptable carrier so as to provide the form for proper administration to the patient. The formulation should suit the mode of administration.

The pharmaceutical compositions of the present invention may be administered by any particular route of administration including, but not limited to oral, parenteral, subcutaneous, intramuscular, intravenous, intrarticular, intrabronchial, intraabdominal, intracapsular, intracartilaginous, intracavitary, intracelial, intracelebellar, intracerebroventricular, intracolic, intracervical, intragastric, intrahepatic, intramyocardial, intraosteal, intraosseous, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, iontophoretic means, or transdermal means. Most suitable routes are oral administration or injection.

In general, the pharmaceutical compositions comprising cholesterol may be used alone or in concert with other therapeutic agents at appropriate dosages defined by routine testing in order to obtain optimal efficacy while minimizing any potential toxicity. The dosage regimen utilizing a pharmaceutical composition of the present invention may be selected in accordance with a variety of factors including type, species, age, weight, sex, medical condition of the patient; the severity of the condition to be treated; the route of administration; the renal and hepatic function of the patient; and the particular pharmaceutical composition employed. A physician of ordinary skill can readily determine and prescribe the effective amount of the pharmaceutical composition (and potentially other agents including therapeutic agents) required to prevent, counter, or arrest the progress of the condition.

Doses of a pharmaceutical composition of the present invention can optionally include about 0.1 mg to about 1,000 mg/kg/administration, or about 1 mg to about 500.0 mg/kg/administration, from about 10 mg to about 400 mg/kg/administration, from about 10 mg to about 300 mg/kg/administration, including, but not limited to, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 and/or 100-500 mg/kg/administration or any range, value or fraction thereof.

As a non-limiting example, treatment of patients can be provided as a one-time or periodic dosage of a composition of the present invention of about 0.1 mg to about 500 mg/kg such as about 0.1 0.5, 0.9, 1.0, 1.1, 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 100, 125, 150, 175, 200, 225, 250, 275, 300, 325, 350, 375, 400, 425, 450, 475 or about 500 mg/kg, per day, on at least one of day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or any combination thereof, using single or repeated doses.

Specifically, the pharmaceutical compositions of the present invention may be administered at least once a week over the course of several weeks. In one embodiment, the pharmaceutical compositions are administered at least once a week over several weeks to several months. In another embodiment, the pharmaceutical compositions are administered once a week over four to eight weeks. In yet another embodiment, the pharmaceutical compositions are administered once a week over four weeks.

More specifically, the pharmaceutical compositions may be administered at least once a day for about 2 days, at least once a day for about 3 days, at least once a day for about 4 days, at least once a day for about 5 days, at least once a day for about 6 days, at least once a day for about 7 days, at least once a day for about 8 days, at least once a day for about 9 days, at least once a day for about 10 days, at least once a day for about 11 days, at least once a day for about 12 days, at least once a day for about 13 days, at least once a day for about 14 days, at least once a day for about 15 days, at least once a day for about 16 days, at least once a day for about 17 days, at least once a day for about 18 days, at least once a day for about 19 days, at least once a day for about 20 days, at least once a day for about 21 days, at least once a day for about 22 days, at least once a day for about 23 days, at least once a day for about 24 days, at least once a day for about 25 days, at least once a day for about 26 days, at least once a day for about 27 days, at least once a day for about 28 days, at least once a day for about 29 days, at least once a day for about 30 days, or at least once a day for about 31 days.

Alternatively, the pharmaceutical compositions may be administered about once every day, about once every 2 days, about once every 3 days, about once every 4 days, about once every 5 days, about once every 6 days, about once every 7 days, about once every 8 days, about once every 9 days, about once every 10 days, about once every 11 days, about once every 12 days, about once every 13 days, about once every 14 days, about once every 15 days, about once every 16 days, about once every 17 days, about once every 18 days, about once every 19 days, about once every 20 days, about once every 21 days, about once every 22 days, about once every 23 days, about once every 24 days, about once every 25 days, about once every 26 days, about once every 27 days, about once every 28 days, about once every 29 days, about once every 30 days, or about once every 31 days.

In specific embodiments, cholesterol supplementation can vary from about 20 to about 300 mg/Kg body weight/day. In more specific embodiments, cholesterol treatment can be about 40 to about 250 mg/Kg body weight/day, about 60 to about 200 mg/Kg body weight/day, about 80 to about 180 mg/Kg body weight/day, about 100 to about 160 mg/Kg body weight/day, or about 120 to about 140 mg/Kg body weight/day.

The pharmaceutical compositions may further be combined with one or more additional therapeutic agents. The determination of the identity and amount of the pharmaceutical compositions for use in the methods of the present invention can be readily made by ordinarily skilled medical practitioners using standard techniques known in the art. In other specific embodiments, cholesterol can be administered in combination with an effective amount of a cholesterol marker (Apo A-l, Apo B, Lipoprotein (a), and/or Homocysteine), a therapeutic agent for medical conditions frequently associated with ASD (e.g., anxiety, depression, attention deficit/hyperactivity disorder, gastrointestinal problems, sleep disturbances and/or epilepsy) or another therapeutic agent.

Without further elaboration, it is believed that one skilled in the art, using the preceding description, can utilize the present invention to the fullest extent. The following examples are illustrative only, and not limiting of the remainder of the disclosure in any way whatsoever.

EXAMPLES

The following examples are put forth so as to provide those of ordinary skill in the art with a complete disclosure and description of how the compounds, compositions, articles, devices, and/or methods described and claimed herein are made and evaluated, and are intended to be purely illustrative and are not intended to limit the scope of what the inventors regard as their invention. Efforts have been made to ensure accuracy with respect to numbers (e.g., amounts, temperature, etc.) but some errors and deviations should be accounted for herein. Unless indicated otherwise, parts are parts by weight, temperature is in degrees Celsius or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

The present inventors aim to establish the frequency of low cholesterol in simplex ASD (where there is only one child with ASD in the family), to better characterize the phenotype of such children, and to carry out a clinical trial of a compound that raises plasma cholesterol and has proven effective in SLOS. Thus, this study tests the hypothesis that cholesterol plays an important role in some children with ASD.

Example 1

A Retrospective Analysis of Rate of Change in Current State ADI Scores in 6 Subjects with Smith-Lemli-Opitz Syndrome Before and after Cholesterol Supplementation was Initiated The variables listed in the analysis of the primary outcomes are below. i=1, . . . , 6 children, j=2, 3 visits socialch$_{ij}$=average change in social measure per year for child i between age at visit j and age at visit j−1. (More specifically, socialch$_{ij}$ is social score at visit j minus social score at visit j−1, divided by the number of years between visits j and j−1.)

verbalch$_{ij}$=average change in verbal measure per year for child i between age at visit j and age at visit j−1.

nonverbalch$_{ij}$=average change in nonverbalch$_{ij}$ measure per year for child i between age at visit j and age at visit j−1.

repetch$_{ij}$=average change in repetitive measure per year for child i between age at visit j and age at visit j−1.

age$_{ij}$=age of child i at visit j at which measure was performed agedif$_{ij}$=number of years between visit j and visit j−1 agechol$_{ij}$=age at which cholesterol supplementation began for child i chol$_{ij}$=1 if cholesterol supplementation has occurred at prior to visit j for child i.

Note that the large improvements are consistent with large negative values. In other words, if a child has a large improvement in social score between visits j−1 and j, this will be reflected as a large negative value for socialch$_{ij}$.

So, the idea is to model the average change in scores before and after supplementation, adjusting for age, the number of years between visits, and the age at which supplementation occurred. To do this, our linear model for "social" is $$socialch_{ij} = \beta_{0i} + \beta_2 age_{ij} + \beta_2 agedif_{ij} + \beta_3 agechol_{ij} + \beta_4 chol_{ij} + e_{ij}$$

We use a linear regression model that allows for correlation between observations from the same individual. Using this model, we estimate the ∃ parameters in the model, which measure the direction and magnitude of the association between social score change and each of the covariates (i.e., age, age difference, age at cholesterol, and cholesterol). The same model was fit for each of the four outcomes. The table below gives the estimated coefficients for each of the 4 primary outcome variables.

TABLE 1

Primary Outcomes

|  |  | Age | Age difference | Age at cholesterol | Cholesterol |
|---|---|---|---|---|---|
| Social | ∃ | 1.12 | −0.027 | −1.07 | −7.07 |
|  | Se(∃) | 0.67 | −0.26 | 0.77 | 2.66 |
|  | Pvalue | 0.10 | 0.92 | 0.16 | 0.008 |
| Verbal | ∃ | 0.95 | −0.69 | −0.13 | −6.97 |
|  | Se(∃) | 0.28 | 0.23 | 0.34 | 1.19 |
|  | Pvalue | 0.001 | 0.002 | 0.71 | <0.001 |
| Nonverbal | ∃ | 0.16 | −0.15 | 0.03 | −2.51 |
|  | Se(∃) | 0.35 | 0.12 | 0.41 | 1.23 |
|  | Pvalue | 0.65 | 0.23 | 0.94 | 0.04 |
| Repetitive | ∃ | −0.20 | 0.03 | 0.18 | 1.54 |
|  | Se(∃) | 0.12 | 0.04 | 0.14 | 0.40 |
|  | Pvalue | 0.08 | 0.40 | 0.19 | <0.001 |

I will interpret the results for the social model only as an example. The age effect is 1.12. This means that there is a positive association between age and change: older children are more likely to positive increases in their rate. Specifically, if we compare two children whose ages differ by 1 year, the older child's change rate is expected to be larger by 1.12 as compared to the younger child's rate. Note that improvements are consistent with negative changes, so this means that older children tend to show less improvement. The standard error of the effect is 0.67 and the associated pvalue is 0.10, suggesting marginal statistical significance.

The age difference effect is −0.027. This implies that there is essentially no association between social score change and the interval of time between visits. But, for purposes of interpretation, we can say that comparing two children whose age intervals between visits differ by one year, the child with the larger interval is likely to have a lower social change rate. So, larger intervals are associated greater improvement. The standard error of this effect is relatively large (0.26) and the pvalue indicates insignificance (p=0.92).

The age at cholesterol effect is estimated to be −1.07. This suggests that there is a negative association between age at cholesterol and social change score. In other words, children who begin supplementation later tend to have greater improvements. For example, if we compare two children whose ages differ by 1 year, if the child who has early supplementation has social change rate of Y, then the child who has later supplementation is expected to have social change score of Y−1.07. This is not consistent with the hypothesis that earlier supplementation proves beneficial. However, statistical significance is not achieved (p=0.16), and the effect size is small.

The last parameter is of primary interest. The cholesterol effect is estimated to be −7.07. This implies that comparing two children of the same age, etc., one of whom is on cholesterol and the other who is not, the child on cholesterol supplementation will have a much steeper negative change rate (i.e. 7.07) than the child not on supplementation. This is statistically significant: p=0.008. In other words, children on cholesterol supplementation improve by an average of 7.07 points year more than children not on supplementation.

TABLE 2

Leaving Out Age At Cholesterol

|  |  | Age | Age difference | Cholesterol |
|---|---|---|---|---|
| Social | ∃ | 0.21 | −0.16 | −5.14 |
|  | Se(∃) | 0.16 | 0.25 | 2.29 |
|  | Pvalue | 0.20 | 0.54 | 0.02 |
| Verbal | ∃ | 0.87 | −0.70 | −6.77 |
|  | Se(∃) | 0.19 | 0.23 | 1.06 |
|  | Pvalue | <0.001 | 0.002 | <0.001 |
| Nonverbal | ∃ | 0.18 | −0.14 | −2.56 |
|  | Se(∃) | 0.08 | 0.11 | 1.00 |
|  | Pvalue | 0.02 | 0.20 | 0.01 |
| Repetitive | ∃ | −0.05 | 0.06 | 1.23 |
|  | Se(∃) | 0.03 | 0.04 | 0.37 |
|  | Pvalue | 0.05 | 0.18 | 0.001 |

TABLE 3

Leaving Out Age Difference From Last Visit

|  |  | Age | Age at chol | Cholesterol |
|---|---|---|---|---|
| Social | ∃ | 1.13 | −1.11 | −6.97 |
|  | Se(∃) | 0.67 | 0.73 | 2.44 |
|  | Pvalue | 0.09 | 0.13 | 0.004 |
| Verbal | ∃ | 0.51 | −0.08 | −4.14 |
|  | Se(∃) | 0.37 | 0.46 | 1.28 |
|  | Pvalue | 0.17 | 0.87 | 0.001 |
| Nonverbal | ∃ | 0.26 | −0.16 | −2.05 |
|  | Se(∃) | 0.36 | 0.40 | 1.28 |
|  | Pvalue | 0.48 | 0.68 | 0.11 |
| Repetitive | ∃ | −0.23 | 0.23 | 1.45 |
|  | Se(∃) | 0.11 | 0.13 | 0.40 |
|  | Pvalue | 0.04 | 0.07 | <0.001 |

The cholesterol effect is consistent across models. Although some collinearity is present, it doesn't appear to drastically change effect sizes across models. There is little to no evidence that age at cholesterol affects improvement in scores.

Example 2

Establish the Prevalence of Hypercholesterolemia and Hypercholesterolemia in an ASD Population without Known Cholesterol Disorders In the process of screening for the 60 individuals with ASD+hypo who will enter the clinical trial, the present inventors are able to estimate the prevalence of hypocholesterolemia and hypercholesterolemia in up to 800 individuals with ASD. This knowledge helps to provide evidence as to which, if not all, individuals with ASD should undergo routine cholesterol testing.

Hypocholesterolemia is defined as more than two standard deviations below the age- and gender-specific cholesterol levels in the typical populations of the CDC National Health and Nutrition Examination Survey (NHANES 2006). Such children are categorized as having both ASD and hypocholesterolemia ("ASD+hypo"); those with hypercholesterolemia as more than two standard deviations above the age- and gender-specific cholesterol levels the NHANES study (ASD+hyper). Subjects who have cholesterol levels between the $41^{st}$ to $60^{th}$ centile of the NHANES study are hereafter referred to as "ASD+4160CHL."

Example 3

Determine the Rate of SLOS in the Hypocholesterolemic Subjects

The individuals with ASD+hypo are screened for SLOS and other disorders of sterol precursors. This step ensures that no ASD+hypo subject that enters the clinical trial has SLOS, and alerts the present inventors to work with the caretaker of a child diagnosed with SLOS or other sterol precursor disorders to establish appropriate medical care.

Example 4

Compare the Behavioral, Physical, and Medical Phenotype of ASD Individuals

The phenotypes of a) 60 individuals with ASD+hypo; b) 60 age-, and gender-matched ASD+hyper; and c) 60 age-, and gender-matched ASD+4160CHL are compared. The identification of any particular features of autistic children with abnormal cholesterol aids in the development of criteria that could be used to determine which autistic children should be screened for sterol abnormalities. The phenotypic characterization also serves as the baseline measurement for the 60 ASD+hypo children who join the clinical trial.

Example 5S

Clinical Trial

A randomized, double-masked placebo-controlled trial of CHL supplementation in 60 children with idiopathic autism who also have ASD+hypo is conducted. This trial provides evidence as to whether cholesterol supplementation alleviates ASD-related symptoms and is safe to use.

We claim:

1. A method for treating a patient having ASD but not SLOS comprising the step of administering a therapeutically effective amount of cholesterol to the patient.

2. A method for treating a patient having ASD, normal cholesterol levels, and who does not have SLOS comprising the step of administering a therapeutically effective amount of cholesterol to the patient.

3. A method for treating a patient having ASD, low cholesterol levels, and who does not have SLOS comprising the step of administering a therapeutically effective amount of cholesterol to the patient.

4. The method of claim 1, wherein the ASD is autism, Asperger's disorder, pervasive developmental disorder-not otherwise specified (PDD-NOS), Rett's syndrome and childhood disintegrative disorder.

5. The method of claim 1, wherein the patient has autism.

6. The method of claim 1, wherein the therapeutically effective amount of cholesterol is about 20 to about 300 mg/Kg body weight/day.

7. The method of claim 1, wherein the patient has clinically low levels of cholesterol.

8. The method of claim 1, wherein the patient has normal cholesterol levels.

9. A method for treating a patient suffering from autism but not SLOS comprising the step of administering a therapeutically effective amount of cholesterol to the patient.

10. A method for treating a patient who has autism, normal cholesterol levels, and who does not have SLOS comprising the step of administering a therapeutically effective amount of cholesterol to the patient.

11. A method for treating a patient who has autism, low cholesterol levels, and who does not have SLOS comprising the step of administering a therapeutically effective amount of cholesterol to the patient.

12. The method of claim 9, wherein the therapeutically effective amount of cholesterol is about 20 to about 300 mg/Kg body weight/day.

13. The method of claim 9, wherein the patient has clinically low levels of cholesterol.

14. The method of claim 9, wherein the patient has normal cholesterol levels.

* * * * *